(12) United States Patent
Koide

(10) Patent No.: US 11,234,578 B2
(45) Date of Patent: Feb. 1, 2022

(54) RECEIVING APPARATUS AND RADIO WAVE INTERFERENCE DETERMINATION METHOD

(71) Applicant: OLYMPUS CORPORATION, Tokyo (JP)

(72) Inventor: Naoto Koide, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 526 days.

(21) Appl. No.: 16/199,361

(22) Filed: Nov. 26, 2018

(65) Prior Publication Data

US 2019/0090721 A1 Mar. 28, 2019

Related U.S. Application Data

(63) Continuation of application No. PCT/JP2017/011280, filed on Mar. 21, 2017.

(30) Foreign Application Priority Data

May 31, 2016 (JP) .............................. JP2016-108859

(51) Int. Cl.
*A61B 1/04* (2006.01)
*A61B 1/00* (2006.01)
(Continued)

(52) U.S. Cl.
CPC ........ *A61B 1/00016* (2013.01); *A61B 1/0002* (2013.01); *A61B 1/00004* (2013.01);
(Continued)

(58) Field of Classification Search
CPC ............ A61B 1/00016; A61B 1/00004; A61B 1/00006; A61B 1/00002; A61B 1/041;
(Continued)

(56) References Cited

U.S. PATENT DOCUMENTS

2004/0162100 A1 8/2004 Moon et al.
2009/0051762 A1 2/2009 Shigemori et al.
(Continued)

FOREIGN PATENT DOCUMENTS

JP 2004-247970 A 9/2004
JP 2006-026299 A 2/2006
(Continued)

OTHER PUBLICATIONS

International Search Report dated Jun. 13, 2017 issued in PCT/JP2017/011280.

(Continued)

*Primary Examiner* — Hesham K Abouzahra
(74) *Attorney, Agent, or Firm* — Scully, Scott, Murphy & Presser, P.C.

(57) ABSTRACT

A receiving apparatus includes: an antenna configured to receive, by a radio wave, an image signal acquired by a capsule-type endoscope; a memory configured to store a determination table or a determination function, each being used for determining an interference level of the radio wave; and a processor comprising hardware, the processor is configured to: acquire a received signal strength of the image signal received by the antenna; generate determination information used for determining the interference level of the radio wave based on one or more synchronization signals included in the image signal; determine the interference level of the radio wave based on the received signal strength and the determination information by using the determination table or the determination function; and control to output information indicating that electromagnetic interference occurs, when the determined interference level of the radio wave is greater than a preset interference level.

7 Claims, 11 Drawing Sheets

(51) Int. Cl.
*A61B 1/045* (2006.01)
*G16H 30/20* (2018.01)
*A61B 5/00* (2006.01)
*H04N 7/18* (2006.01)
*H04N 5/067* (2006.01)

(52) U.S. Cl.
CPC .......... *A61B 1/00006* (2013.01); *A61B 1/041* (2013.01); *A61B 1/045* (2013.01); *A61B 5/0031* (2013.01); *G16H 30/20* (2018.01); *H04N 7/18* (2013.01); *H04N 7/183* (2013.01); *A61B 1/00009* (2013.01); *H04N 5/0675* (2013.01)

(58) Field of Classification Search
CPC ...... A61B 1/045; A61B 5/0031; G16H 30/20; H04N 7/18; H04N 7/183
See application file for complete search history.

(56) References Cited

U.S. PATENT DOCUMENTS

| | | | |
|---|---|---|---|
| 2011/0193949 | A1* | 8/2011 | Nambakam ............ A61B 17/00 348/74 |
| 2012/0200688 | A1 | 8/2012 | Endo et al. |
| 2013/0158344 | A1* | 6/2013 | Taniguchi .......... A61B 1/00006 600/103 |

FOREIGN PATENT DOCUMENTS

| | | |
|---|---|---|
| JP | 2007-075161 A | 3/2007 |
| JP | 2012-253807 A | 12/2012 |
| WO | WO 2012/137705 A1 | 10/2012 |

OTHER PUBLICATIONS

Japanese Notification of Reasons for Refusal dated Jun. 26, 2018 issued in JP 2017-549438.

* cited by examiner

FIG.3

| RSSI | \ NUMBER OF SYNCHRONIZATION SIGNALS ACQUIRED | | | | | | | | | | | |
|---|---|---|---|---|---|---|---|---|---|---|---|---|
| | 0 TO 20 | 21 TO 40 | 41 TO 60 | 61 TO 80 | 81 TO 100 | 101 TO 120 | 121 TO 140 | 161 TO 180 | 181 TO 200 | 201 TO 220 | 221 TO 240 | 241 TO |
| 0 TO 3000 | 0 | 0 | 0 | 0 | 0 | 0 | 0 | 0 | 0 | 0 | 0 | 0 |
| 3001 TO 6000 | 0 | 0 | 0 | 0 | 0 | 0 | 0 | 0 | 0 | 0 | 0 | 0 |
| 6001 TO 9000 | 0 | 0 | 0 | 0 | 0 | 0 | 0 | 0 | 0 | 0 | 0 | 0 |
| 9001 TO 12000 | 0 | 0 | 0 | 0 | 0 | 0 | 0 | 0 | 0 | 0 | 0 | 0 |
| 12001 TO 15000 | 1 | 0 | 0 | 0 | 0 | 0 | 0 | 0 | 0 | 0 | 0 | 0 |
| 15001 TO 18000 | 1 | 1 | 1 | 0 | 0 | 0 | 0 | 0 | 0 | 0 | 0 | 0 |
| 18001 TO 21000 | 1 | 1 | 1 | 1 | 1 | 0 | 0 | 0 | 0 | 0 | 0 | 0 |
| 21001 TO 24000 | 2 | 1 | 1 | 1 | 1 | 1 | 1 | 0 | 0 | 0 | 0 | 0 |
| 24001 TO 27000 | 2 | 2 | 2 | 2 | 1 | 1 | 1 | 1 | 0 | 0 | 0 | 0 |
| 27001 TO 30000 | 2 | 2 | 2 | 2 | 2 | 1 | 1 | 1 | 0 | 0 | 0 | 0 |
| 30001 TO 33000 | 3 | 2 | 2 | 2 | 2 | 2 | 1 | 1 | 1 | 1 | 0 | 0 |
| 33001 TO 36000 | 3 | 3 | 2 | 2 | 2 | 2 | 2 | 1 | 1 | 1 | 0 | 0 |
| 36001 TO 39000 | 3 | 3 | 3 | 3 | 3 | 2 | 2 | 1 | 1 | 1 | 1 | 0 |
| 42001 TO 45000 | 4 | 3 | 3 | 3 | 3 | 2 | 2 | 2 | 1 | 1 | 1 | 0 |
| 48001 TO 51000 | 4 | 4 | 3 | 3 | 3 | 3 | 2 | 2 | 2 | 1 | 1 | 0 |
| 51001 TO 54000 | 4 | 4 | 4 | 4 | 3 | 3 | 2 | 2 | 2 | 2 | 1 | 0 |
| 54001 TO 57000 | 5 | 4 | 4 | 4 | 4 | 3 | 3 | 2 | 2 | 2 | 1 | 0 |
| 57001 TO 60000 | 5 | 5 | 4 | 4 | 4 | 3 | 3 | 3 | 2 | 2 | 2 | 0 |
| 60000 TO | 5 | 5 | 5 | 4 | 4 | 4 | 3 | 3 | 3 | 2 | 2 | 0 |

RECEIVING APPARATUS AND RADIO WAVE INTERFERENCE DETERMINATION METHOD

CROSS-REFERENCE TO RELATED APPLICATION

This application is a continuation of PCT International Application No. PCT/JP2017/011280 filed on Mar. 21, 2017, which claims the benefit of priority from Japanese Patent Application No. 2016-108859, filed on May 31, 2016, the entire contents of which are incorporated herein by reference.

BACKGROUND

The present disclosure relates to: a receiving apparatus that receives a radio signal transmitted from a capsule-type endoscope introduced into a subject; and a radio wave interference determination method for determination of an interference level of a radio wave between a capsule-type endoscope and a receiving device.

Endoscopes have been in widespread use as medical observation devices, which are introduced into bodies of subjects, such as patients, and which are for observation of the interiors of the subjects. Further, a capsule-type endoscope has been developed recently, which is a swallowing-type image acquisition device including, inside a capsule casing: an imaging device; and a communication device that wirelessly transmits, to the outside of a body, an image signal captured by the imaging device. The capsule-type endoscope has a function of moving inside organs, such as, for example, the esophagus, the stomach, and the small intestine, according to peristaltic movement of the organs, and sequentially capturing images therein, after being swallowed from the mouth of the patient for observation of the interior of the subject, until the capsule-type endoscope is naturally excreted from the subject.

Image signals captured by the capsule-type endoscope while the capsule-type endoscope is moving inside the subject are sequentially transmitted to the outside of the body by radio communication, and are accumulated in a memory provided inside or outside a receiving device that is outside the body, or are displayed as images on a display provided in the receiving device. A doctor or a nurse is able to: fetch the image signals accumulated in the memory, into an information processing apparatus via a cradle having the receiving device inserted therein; and make diagnoses based on images displayed on a display of this information processing apparatus.

A technique has been known, in which the number of synchronization signals in one frame is detected, and when the detected number is greater than a predetermined value, the image of that frame is deleted (as seen in, for example, Japanese Patent Application Laid-open No. 2007-075161). According to this technique, by acquisition of only images with less noise, quality of images captured by a capsule-type endoscope is able to be maintained.

SUMMARY

A receiving device according to one aspect of the present disclosure includes: an antenna configured to receive, by a radio wave, an image signal acquired by a capsule-type endoscope; a memory configured to store a determination table or a determination function, each being used for determining an interference level of the radio wave; and a processor comprising hardware, the processor is configured to: acquire a received signal strength of the image signal received by the antenna; generate determination information used for determining the interference level of the radio wave based on one or more synchronization signals included in the image signal; determine the interference level of the radio wave based on the received signal strength and the determination information by using the determination table or the determination function; and control to output information indicating that electromagnetic interference occurs, when the determined interference level of the radio wave is greater than a preset interference level.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a diagram for explanation of an interference level determination table stored in a storage unit of the capsule-type endoscope system according to the first embodiment;

DETAILED DESCRIPTION

Hereinafter, as embodiments according to the present disclosure, capsule-type endoscope systems that use medical capsule-type endoscopes will be described. The same reference signs will each be assigned to portions that are the same, throughout the drawings. Further, the drawings are schematic, and a relation between a thickness and a width of each member and ratios among the members may be different from the actual relation and ratios.

First Embodiment

Figure 1:
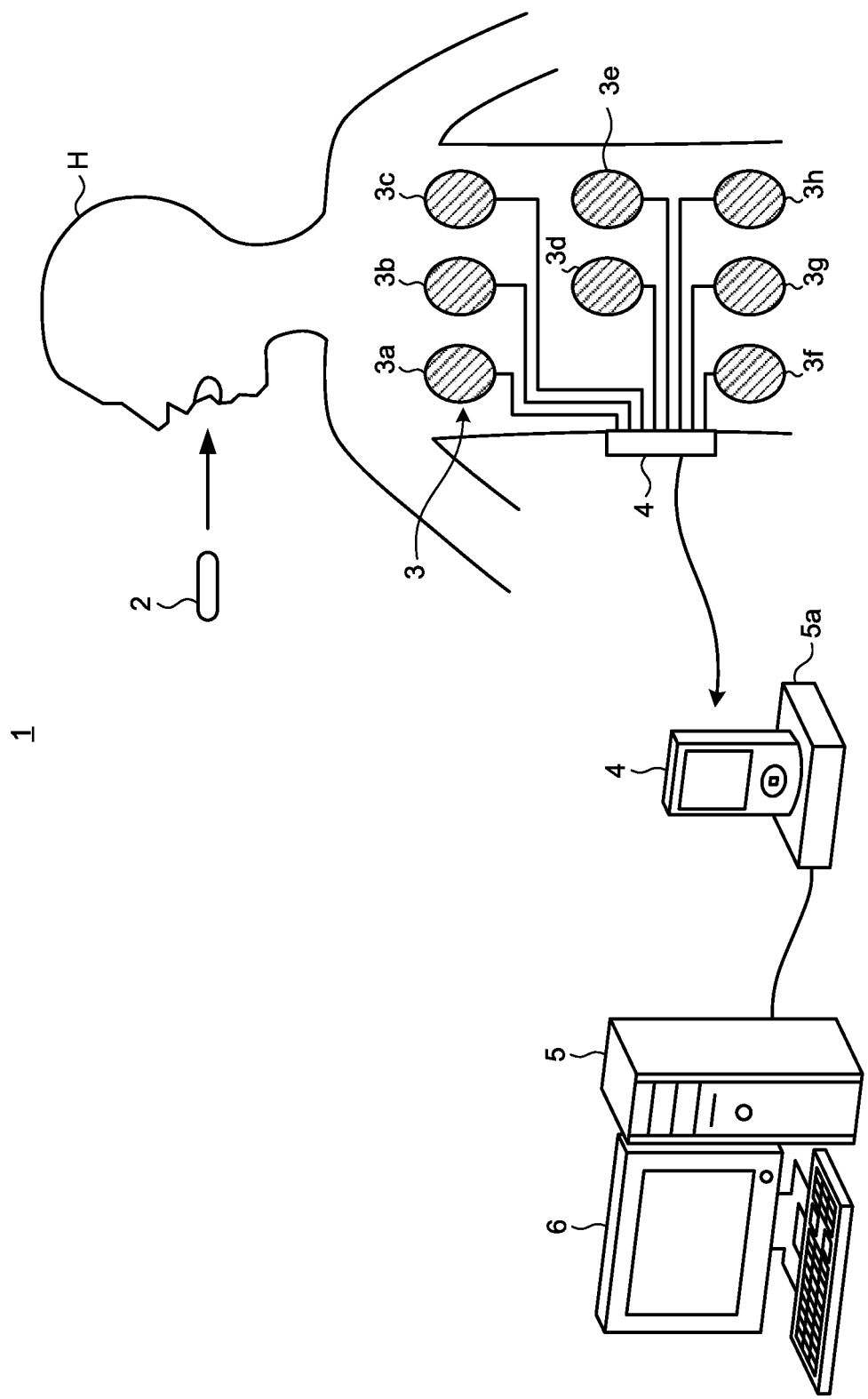
FIG. 1 is a schematic diagram illustrating a schematic configuration of a capsule-type endoscope system according to a first embodiment.

FIG. 1 is a schematic diagram illustrating a schematic configuration of a capsule-type endoscope system according to a first embodiment. As illustrated in FIG. 1, a capsule-type endoscope system 1 according to the first embodiment includes: a capsule-type endoscope 2, which is an image acquisition device that is introduced into a subject H, generates an image signal by imaging the interior of the subject H, superimposes the image signal on a radio signal, and transmits the superimposed signal via a radio wave; a receiving device 4 that receives the radio signal transmitted from the capsule-type endoscope 2 via a receiving antenna unit 3 including plural receiving antennas 3a to 3h attached to the subject H; and a processing device 5 that fetches the image signal captured by the capsule-type endoscope 2 from the receiving device 4 via a cradle 5a, processes the image signal, and generates an in-vivo image of the subject H. The image generated by the processing device 5 is, for example, output from a display device 6 by being displayed thereon. The receiving antenna unit 3 and the receiving device 4 are structural elements of a receiving apparatus according to the present disclosure.

Figure 2:
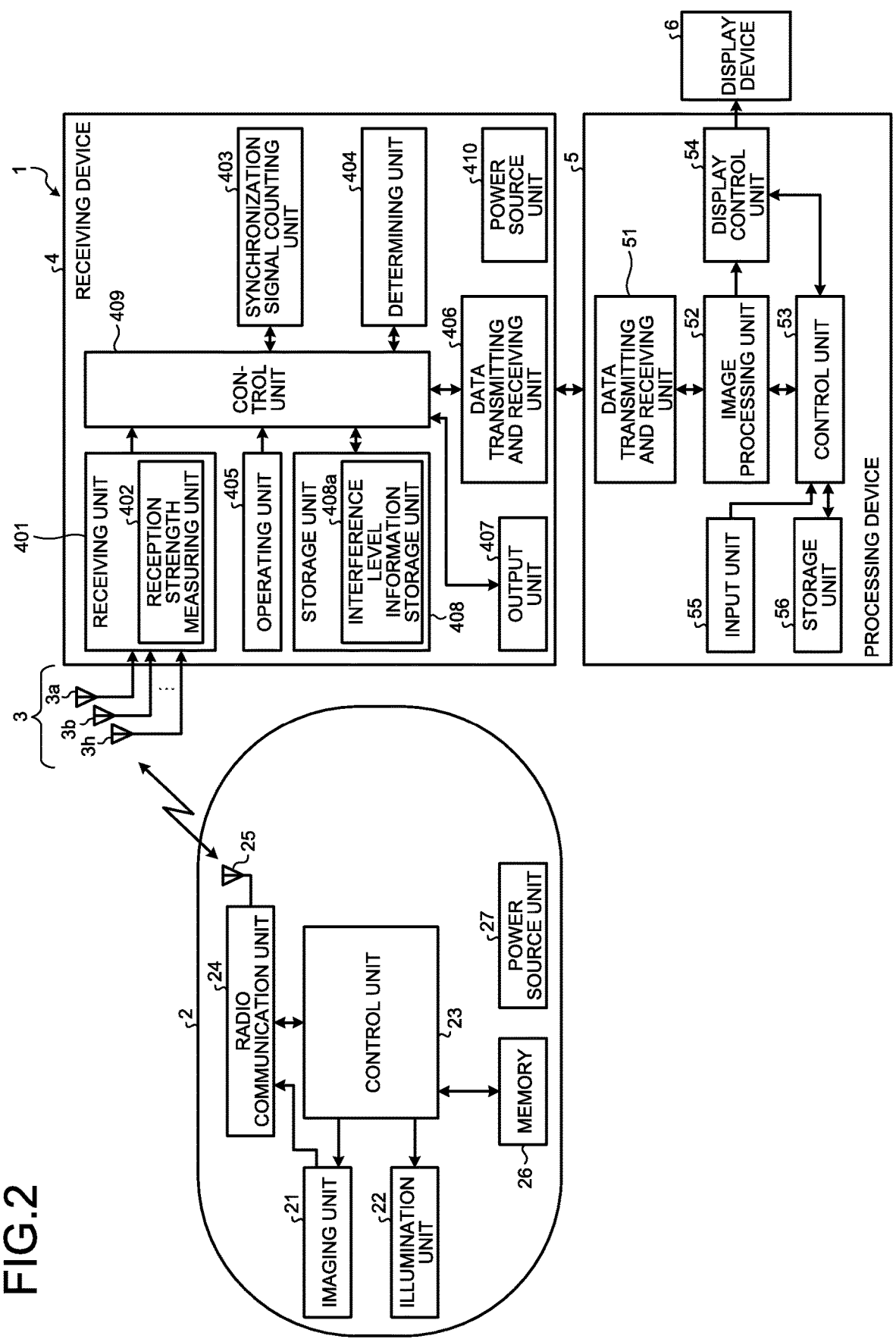
FIG. 2 is a block diagram illustrating a schematic configuration of the capsule-type endoscope system according to the first embodiment.

FIG. 2 is a block diagram illustrating a schematic configuration of the capsule-type endoscope system according to the first embodiment. The capsule-type endoscope 2 includes an imaging unit 21, an illumination unit 22, a control unit 23, a radio communication unit 24, an antenna 25, a memory 26, and a power source unit 27. The capsule-type endoscope 2 is a device having various built-in components in a capsule-shaped casing having a size swallowable by the subject H.

The imaging unit 21 includes, for example: an imaging element that generates an image signal obtained by imaging of the interior of the subject H, from an optical image formed on a light receiving surface, and that outputs the image signal; and an optical system, such as an objective lens, which is arranged on a light receiving surface side of the imaging element. The imaging element is formed of a CCD imaging element or a CMOS imaging element, has plural pixels that receive light from the subject H, the plural pixels being arranged in a matrix, and generates an image signal by performing photoelectric conversion of the light received by the pixels. For the plural pixels arranged in a matrix, the imaging unit 21 reads out pixel values per horizontal line, and generates an image signal including plural sets of line data having a synchronization signal allocated to each horizontal line.

The illumination unit 22 is formed of a white LED that generates white light serving as illumination light. Instead of being formed of a white LED, the illumination unit 22 may be configured to generate white light by combining light of plural LEDs or laser light sources that have different emission wavelength bands, or may be configured by use of a xenon lamp or a halogen lamp.

The control unit 23 controls operation and processing of each component of the capsule-type endoscope 2. When, for example, the imaging unit 21 performs imaging processing; the control unit 23 controls the imaging unit 21 to execute exposure and reading processing for the imaging element, and controls the illumination unit 22 to emit the illumination light according to the exposure timing of the imaging unit 21. The control unit 23 is configured by use of a general-purpose processor, such as a central processing unit (CPU), or a special-purpose processor, such as any of various arithmetic circuits that each execute a specific function, like application specific integrated circuits (ASICs).

The radio communication unit 24 processes the image signal output from the imaging unit 21. The radio communication unit 24 acquires a digital image signal by performing A/D conversion and predetermined signal processing on the image signal output from the imaging unit 21, superimposes the digital image signal, together with related information, on a radio signal, and transmits the superimposed signal to outside, from the antenna 25. The related information includes identification information (for example, a serial number) that has been allocated for identification of the individuality of the capsule-type endoscope 2.

The memory 26 stores therein an execution program and a control program for the control unit 23 to execute various operations. Further, the memory 26 may temporarily store therein the image signal that has been signal-processed in the radio communication unit 24. The memory 26 is formed of a RAM and a ROM.

The power source unit 27 includes: a battery formed of, for example, a button cell; a power source circuit that boosts the electric power from the battery; and a power source switch that switches the power source unit 27 between an on-state and an off-state; and the power source unit 27 supplies electric power to each unit in the capsule-type endoscope 2 after the power switch is turned on. The power source switch is formed of, for example, a reed switch that is switched over between an on-state and an off-state by external magnetic force, and is switched to the on-state by application of magnetic force from outside to the capsule-type endoscope 2 before use of the capsule-type endoscope 2 (before the subject H swallows the capsule-type endoscope 2).

After being swallowed by the subject H, this capsule-type endoscope 2 sequentially captures images of organs of the living body (the esophagus, the stomach, the small intestine, and the large intestine) at predetermined cycles (for example, at 0.5-second cycles), while moving through the digestive tract of the subject H, according to peristaltic movement of the organs. Image signals and related information acquired by this imaging operation are sequentially transmitted wirelessly to the receiving device 4.

The receiving device 4 includes a receiving unit 401, a reception strength measuring unit 402, a synchronization signal counting unit 403, a determining unit 404, an operating unit 405, a data transmitting and receiving unit 406, an output unit 407, a storage unit 408, a control unit 409, and a power source unit 410 that supplies electric power to each of these units.

The receiving unit 401 receives, via the receiving antenna unit 3 having the plural (eight in FIG. 1) receiving antennas 3a to 3h, the image signals and related information wirelessly transmitted from the capsule-type endoscope 2. Each of the receiving antennas 3a to 3h is realized by use of, for example, a loop antenna or a dipole antenna, and is arranged at a predetermined position on an outer surface of the subject H. The receiving unit 401 has the reception strength measuring unit 402 that measures a received signal strength indicator (RSSI) of an image signal received by the receiving antennas 3a to 3h. Based on the received signal strength indicator measured by the reception strength measuring unit 402, the receiving unit 401 selects an antenna having the highest received signal strength indicator, from the receiving antennas 3a to 3h, and receives an image signal received by the selected antenna. The receiving unit 401 is formed of, for example, a processor, such as a CPU, and performs predetermined signal processing, such as A/D conversion, on the received image signal.

The reception strength measuring unit 402 measures a received signal strength indicator at the time of reception of an image signal by the receiving unit 401, for each of the receiving antennas 3a to 3h. All of the received signal strength indicators that have been measured, and the image signals received by the receiving unit 401 may be stored in association with each other, in the storage unit 408. The reception strength measuring unit 402 corresponds to a strength acquiring unit according to the present disclosure.

The synchronization signal counting unit 403 counts the number of synchronization signals included in an image signal. For an image of one frame, the number of synchronization signals included in the image signal is, for example, about 300. If an image signal has been able to be received unerringly, the synchronization signal counting unit 403 is able to acquire all of the synchronization signals, and thus will count about three hundred synchronization signals therein. On the contrary, if radio wave interference has occurred, all of the synchronization signals are not necessarily able to be acquired unerringly, and the count may become less than 300. The synchronization signal counting unit 403 functions as a determination information generating unit according to the present disclosure, and outputs the number of synchronization signals (the number of synchronization signals acquired), which is determination information according to the present disclosure. The number of synchronization signals, and the image signal received by the receiving unit 401 may be stored in association with each other, in the storage unit 408. The synchronization signal counting unit 403 is formed of a CPU or an ASIC.

Based on the received signal strength indicator measured by the reception strength measuring unit 402, the number of synchronization signals acquired counted by the synchronization signal counting unit 403, and information stored in the storage unit 408, the determining unit 404 determines an interference level between the capsule-type endoscope 2 and the receiving antenna unit 3. Specifically, the determining unit 404 determines the interference level by using an interference level determination table (described later) for determination of the interference level according to a combination of a received signal strength indicator and the number of synchronization signals acquired. The determining unit 404 is formed of a CPU or an ASIC.

The operating unit 405 is an input device that is used when a user inputs various types of setting information and instruction information to the receiving device 4. The operating unit 405 is, for example, switches and buttons provided on an operating panel of the receiving device 4.

The data transmitting and receiving unit 406 transmits the image signal and related information that have been stored in the storage unit 408 to the processing device 5, when the data transmitting and receiving unit 406 is connected to the processing device 5 in a state where the data transmitting and receiving unit 406 is communicatable with the processing device 5. The data transmitting and receiving unit 406 is formed of a communication I/F, such as a LAN.

The output unit 407 is configured to display images, output sound or light, and generate vibration. The output unit 407 is configured to display notification images according to interference levels, and to generate sound, light, or vibration. The output unit 407 is formed of at least one of: a display, such as a liquid crystal display or an organic EL display; a speaker; a light source; and a vibration generator, such as a vibrating motor.

The storage unit 408 stores therein: a program for causing the receiving device 4 to operate and execute various functions; the image signal acquired by the capsule-type endoscope 2; and the number of synchronization signals acquired. The storage unit 408 is formed of a RAM and a ROM. The storage unit 408 has an interference level information storage unit 408a that stores therein information for the determining unit 404 to determine the interference level. The interference level information storage unit 408a stores therein the above mentioned interference level determination table, a trigger condition for output processing according to an interference level, and an image that the output unit 407 displays according to the interference level.

FIG. 3 is a diagram for explanation of the interference level determination table stored in the storage unit of the capsule-type endoscope system according to the first embodiment. The interference level determination table represents, as illustrated in FIG. 3, an interference level distribution determined by received signal strength indicators (RSSIs) and the numbers of synchronization signals acquired. FIG. 3 illustrates an example where about three hundred synchronization signals are counted at most. If the received signal strength indicator is high, there will be few errors in the data, and the synchronization signals will be able to be acquired correctly. On the contrary, if the received signal strength indicator is low, there will be many errors in the data, and the number of synchronization signals that are able to be acquired correctly will be small. Inability to acquire the synchronization signals correctly despite the high received signal strength indicator means that the radio signal is receiving some sort of interference, and thus levels of radio wave interference are able to be expressed by a matrix of received signal strength indicators and the numbers of synchronization signals as illustrated in FIG. 3. At the bottom left of the table in FIG. 3, even though the received signal strength indicator is very high, the synchronization signals are hardly able to be acquired, and it is thus determined that strong radio wave interference has occurred. The determining unit 404 determines an interference level, from the received signal strength indicator and the number of synchronization signals acquired, based on the interference level determination table. The interference level determination table is generated beforehand, based on interference levels determined by RSSIs and the numbers of synchronization signals acquired, which have been measured in advance.

The control unit 409 controls each component of the receiving device 4. The control unit 409 is configured by use of: a general-purpose processor, such as a CPU; or a special-purpose processor, such as an arithmetic circuit that executes a specific function, like an ASIC. The control unit 409 causes output processing to be performed by the output unit 407, according to the interference level determined by the determining unit 404.

The receiving device 4 is attached to and carried by the subject H while imaging is being performed by the capsule-type endoscope 2, for example, while the capsule-type endoscope 2 is passing through the digestive tract after being swallowed by the subject H, until the capsule-type endoscope 2 is excreted. The receiving device 4 causes the storage unit 408 to store therein the image signals received via the receiving antenna unit 3 during the imaging. Further, the receiving device 4 causes the storage unit 408 to store therein the received signal strength indicator measured by the reception strength measuring unit 402, the number of synchronization signals acquired counted by the synchronization signal counting unit 403, and the interference level determined by the determining unit 404, in association with the image signal corresponding thereto.

After the imaging by the capsule-type endoscope 2 is finished, the receiving device 4 is removed from the subject H, and is set in the cradle 5a (see FIG. 1) connected to the processing device 5. Thereby, the receiving device 4 is connected to the processing device 5 in a state communicatable therewith, and the receiving device 4 transfers (downloads) the image signals and related information stored in the storage unit 408, to the processing device 5.

The processing device 5 is configured by use of, for example, a work station including the display device 6, such as a liquid crystal display. The processing device 5 includes a data transmitting and receiving unit 51, an image processing unit 52, a control unit 53 that integrally controls the respective units, a display control unit 54, an input unit 55, and a storage unit 56.

The data transmitting and receiving unit 51 is an interface that is connectable to a USB, or a communication line, such as a wired LAN or a wireless LAN, and includes a USB port and a LAN port. According to this embodiment, the data transmitting and receiving unit 51: is connected to the receiving device 4 via the cradle 5a that is connected to the USB port; and performs transmission and reception of data to and from the receiving device 4.

The image processing unit 52 is formed of a CPU or an ASIC; and by reading a predetermined program stored in the storage unit 56 described later, the image processing unit 52 performs predetermined image processing for generating in-vivo images corresponding to the image signals input from the data transmitting and receiving unit 51 or the image signals stored in the storage unit 56.

The control unit 53 is formed of a general-purpose processor, such as a CPU, or a special-purpose processor, such as an arithmetic circuit that executes a specific function; and by reading various programs stored in the storage unit 56, the control unit 53 performs, based on signals input via the input unit 55 and the image signals input from the data transmitting and receiving unit 51, transfer of instructions and data to the respective units forming the processing device 5, and integrally controls operation of the whole processing device 5.

After performing predetermined processing, such as data thinning and gradation processing, on the images generated in the image processing unit 52, according to an image display range in the display device 6, the display control unit 54 causes the display device 6 to output the processed images by displaying thereon the processed images. The display control unit 54 is formed of a CPU or an ASIC.

The input unit 55 is realized by an input device, such as, for example: a keyboard and a mouse; a touch panel; or various switches. The input unit 55 receives input of information and commands according to operations of a user.

The storage unit 56 is realized by: a semiconductor memory, such as a flash memory, a RAM, or a ROM; or a recording medium, such as an HDD, an MO, a CD-R, or a DVD-R, and a drive device that drives the recording medium. The storage unit 56 stores therein a program for causing the processing device 5 to operate and execute various functions, various kinds of information used during the execution of the program, the image signals and related information acquired via the receiving device 4, and the in-vivo images generated by the image processing unit 52.

Figure 4:
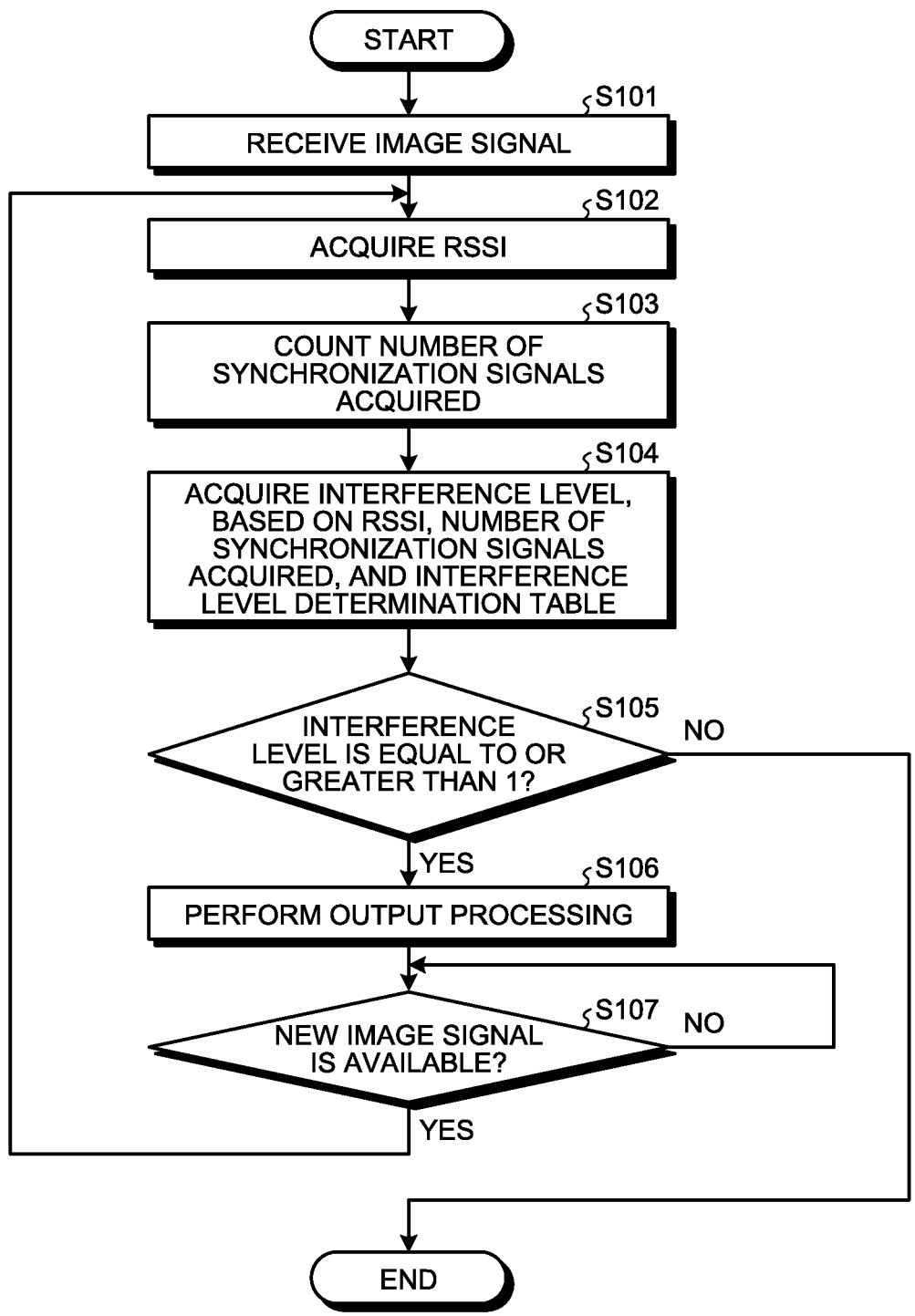
FIG. 4 is a flow chart illustrating interference level determination processing performed by a receiving device of the capsule-type endoscope system according to the first embodiment.

Next, interference level determination processing executed by the receiving device 4 will be described. FIG. 4 is a flow chart illustrating the interference level determination processing performed by the receiving device of the capsule-type endoscope system according to the first embodiment. When the receiving unit 401 receives an image signal, the control unit 409 performs the interference level determination processing. Hereinafter, description will be made on the assumption that each unit operates under control by the control unit 409.

Firstly, at Step S101, the receiving unit 401 receives an image signal.

At Step S102 subsequent to Step S101, the reception strength measuring unit 402 measures a received signal strength indicator at the time of reception of the image signal by the receiving unit 401. The reception strength measuring unit 402 outputs the measured received signal strength indicator, to the determining unit 404.

At Step S103 subsequent to Step S102, the synchronization signal counting unit 403 counts the number of synchronization signals that have been able to be acquired correctly, the synchronization signals being included in the image signal. The synchronization signal counting unit 403 outputs the number of correctly acquired synchronization signals, to the determining unit 404. The order of Step S102 and Step S103 is not limited to the above described order, and thus Step S103 may be performed before Step S102, or Step S102 and Step S103 may be performed simultaneously.

At Step S104 subsequent to Step S103, the control unit 409 acquires an interference level of an image signal to be subjected to determination, which is, in this case, the image signal that has been received this time. Based on the received signal strength indicator measured by the reception strength measuring unit 402, the number of synchronization signals acquired counted by the synchronization signal counting unit 403, and the interference level determination table illustrated in FIG. 3, the determining unit 404 determines an interference level between the capsule-type endoscope 2 and the receiving antenna unit 3, and outputs a result of the determination to the control unit 409.

Thereafter, the control unit 409 determines whether or not to cause the output unit 407 to perform output processing, according to the acquired interference level, and the trigger condition for the output processing, the trigger condition having been stored in the interference level information storage unit 408a. Specifically, the control unit 409 determines whether or not to cause the output unit 407 to perform the output processing, by determining whether or not the interference level is greater than a preset level. In this first embodiment, description will be made on the assumption that a condition has been set, the condition being that the output unit 407 is caused to perform the output processing when the interference level is equal to or greater than 1.

The control unit 409 determines whether or not the interference level is equal to or greater than 1 (Step S105). If the interference level is less than 1 (Step S105: No), the control unit 409 ends the interference level determination processing for the image signal.

On the contrary, if the interference level is equal to or greater than 1 (Step S105: Yes), the control unit 409 proceeds to Step S106.

At Step S106, the control unit 409 causes the output unit 407 to perform the output processing. Under control by the control unit 409, the output unit 407 displays a notification image, and generates sound, light, or vibration, according to the interference level.

Figure 5:
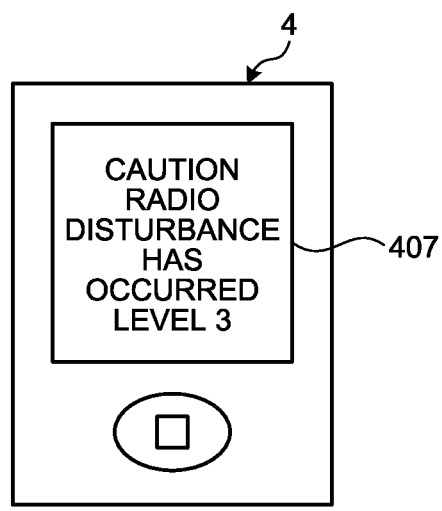
FIG. 5 is a diagram illustrating an example of output processing performed by the receiving device of the capsule-type endoscope system according to the first embodiment.

FIG. 5 is a diagram illustrating an example of output processing performed by the receiving device of the capsule-type endoscope system according to the first embodiment. When the output unit 407 displays the image according to the interference level, as illustrated in FIG. 5, a message indicating that electromagnetic interference has occurred, and the interference level determined this time are displayed on a display screen of the output unit 407. By checking this displayed image, the subject H moves to another place from the current place where the electromagnetic interference has occurred.

The output unit 407 may, in addition to displaying the image, for example, generate sound, light, or vibration. For example, when the output unit 407 generates sound, the output unit 407 may output a constant sound regardless of the interference level, may increase the volume of sound as the interference level is increased, or may change the mode of output of sound according to the interference level. When the output unit 407 outputs light, the output unit 407 may output light at a constant intensity regardless of the interference level, may increase the intensity of light as the interference level is increased, or may change the mode of output of light according to the interference level, for example, the blinking cycle or the color. Similarly, when the output unit 407 generates vibration, the output unit 407 may generate vibration at a constant frequency regardless of the interference level, or may increase the frequency or amplitude as the interference level is increased.

At Step S107 subsequent to Step S106, the control unit 409 determines whether or not a new image signal is available. Specifically, the control unit 409 determines whether or not the receiving unit 401 has received a new image signal. If a new image signal is not available (Step S107: No), the control unit 409 repeats the check for an image signal. On the contrary, if a new image signal is available (Step S107: Yes), the control unit 409 proceeds to Step S102, and performs the above described interference level determination processing for the new image signal.

By the above described determination processing, the subject H having the capsule-type endoscope 2 introduced therein is able to be guided to a place where electromagnetic interference does not occur.

This interference level determination processing may be performed every time reception is done, may be performed at preset intervals, for example, every several frames, or may be performed before or immediately after the subject H swallows the capsule-type endoscope 2.

According to the above described first embodiment, since the determining unit 404 determines, based on a received signal strength indicator acquired by the reception strength measuring unit 402, the number of synchronization signals acquired counted by the synchronization signal counting unit 403, and the interference level determination table, an interference level between the capsule-type endoscope 2 and the receiving antenna unit 3, and gives notification to the subject H based on a result of the determination; interference in communication between the capsule-type endoscope 2 and the receiving device 4 is able to be avoided. Thereby, errors in images generated from image signals wirelessly transmitted from the capsule-type endoscope 2 are able to be reduced, and thus accuracy of diagnoses is able to be improved.

Modified Example of First Embodiment

Figure 6:
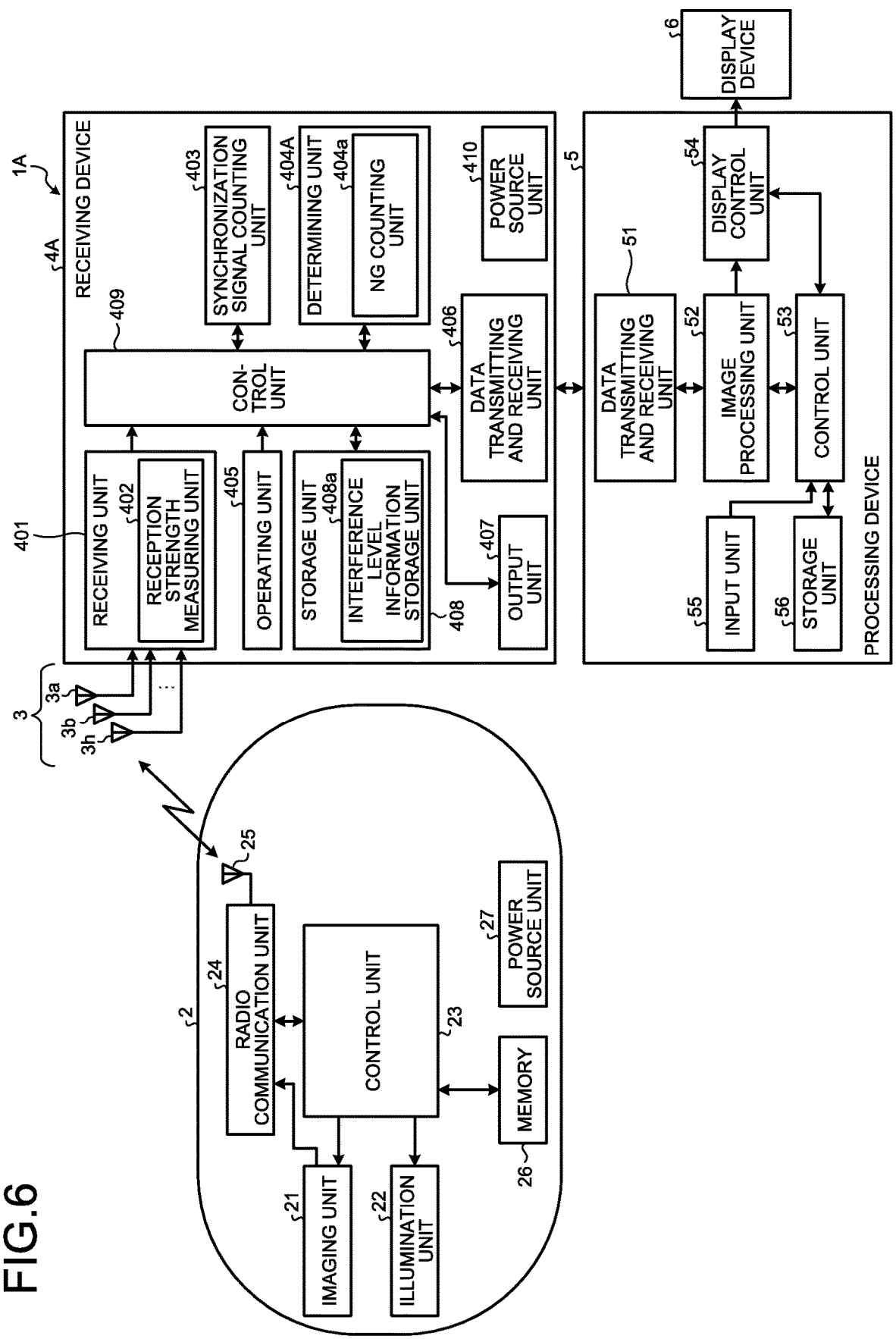
FIG. 6 is a block diagram illustrating a schematic configuration of a capsule-type endoscope system according to a modified example of the first embodiment.

Next, a modified example of the first embodiment will be described. FIG. 6 is a block diagram illustrating a schematic configuration of a capsule-type endoscope system according to the modified example of the first embodiment.

A capsule-type endoscope system 1A according to this modified example includes: the capsule-type endoscope 2; a receiving device 4A that receives, via the receiving antenna unit 3 including the plural receiving antennas 3a to 3h attached to the subject H, a radio signal transmitted from the capsule-type endoscope 2; and the processing device 5 that fetches an image signal captured by the capsule-type endoscope 2 from the receiving device 4A via the cradle 5a, processes the image signal, and generates an in-vivo image of the subject H. The image generated by the processing device 5 is, for example, output from the display device 6 by being displayed thereon.

Among the above described components of the receiving device 4, the receiving device 4A includes, instead of the determining unit 404, a determining unit 404A.

Based on a received signal strength indicator measured by the reception strength measuring unit 402, the number of synchronization signals (the number of synchronization signals acquired) counted by the synchronization signal counting unit 403, and information stored in the storage unit 408, the determining unit 404A determines an interference level between the capsule-type endoscope 2 and the receiving antenna unit 3. The determining unit 404A is formed of a CPU or an ASIC.

In addition to determination of whether or not a synchronization signal has been acquired for each set of line data and counting of the number of synchronization signals that have been able to be acquired, the determining unit 404A includes an NG counting unit 404a that records, when a synchronization signal is not acquired, the number of times where absence of a synchronization signal occurs consecutively. The NG counting unit 404a counts the number of synchronization signals that are not acquired consecutively (hereinafter, "the consecutive number"), and the number of blocks, each in which a certain number or more of synchronization signals are not acquired. The NG counting unit 404a determines the possibility of acquisition of synchronization signals, in the order of the sets of line data, for example, in the order of arrangement of the horizontal lines, and counts the above mentioned consecutive numbers and number of blocks. The NG counting unit 404a may cause the storage unit 408 or the interference level information storage unit 408a to store therein the counted consecutive numbers and number of blocks.

Figure 7:
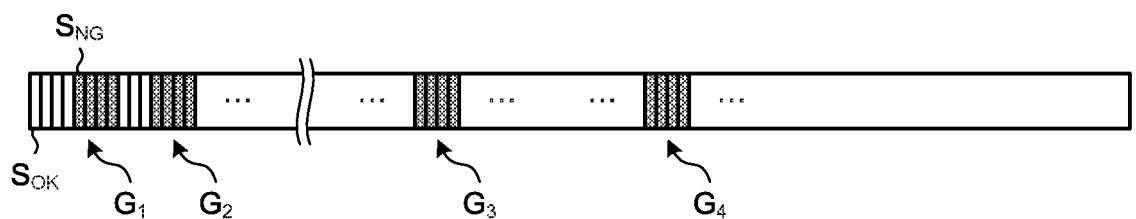
FIG. 7 is a diagram illustrating an image of a state where synchronization signals have been unable to be acquired in the capsule-type endoscope system according to the modified example of the first embodiment.

FIG. 7 is a diagram illustrating an image of a state where synchronization signals have been unable to be acquired in the capsule-type endoscope system according to the modified example of the first embodiment. In FIG. 7, a state where a synchronization signal has been able to be acquired correctly is denoted by $S_{OK}$, and a state where a synchronization signal has been unable to be acquired is denoted by $S_{NG}$. Further, a block where the state $S_{NG}$ lasted consecutively is denoted by $G_N$. In FIG. 7, four blocks (blocks $G_1$ to $G_4$) have been generated.

Firstly, similarly to the above described first embodiment, the determining unit 404A performs determination of an interference level by using the interference level determination table for determination of the interference level based on a combination of a received signal strength indicator and the number of synchronization signals acquired. Thereafter, the determining unit 404A compares the number of times the state $S_{NG}$ lasted consecutively and the number of blocks $G_N$, each in which the state $S_{NG}$ lasted consecutively for a certain number of times or more, these numbers having been recorded by the NG counting unit 404a, with preset thresholds, and performs correction of the interference level if these numbers are equal to or greater than the thresholds.

Figure 8:
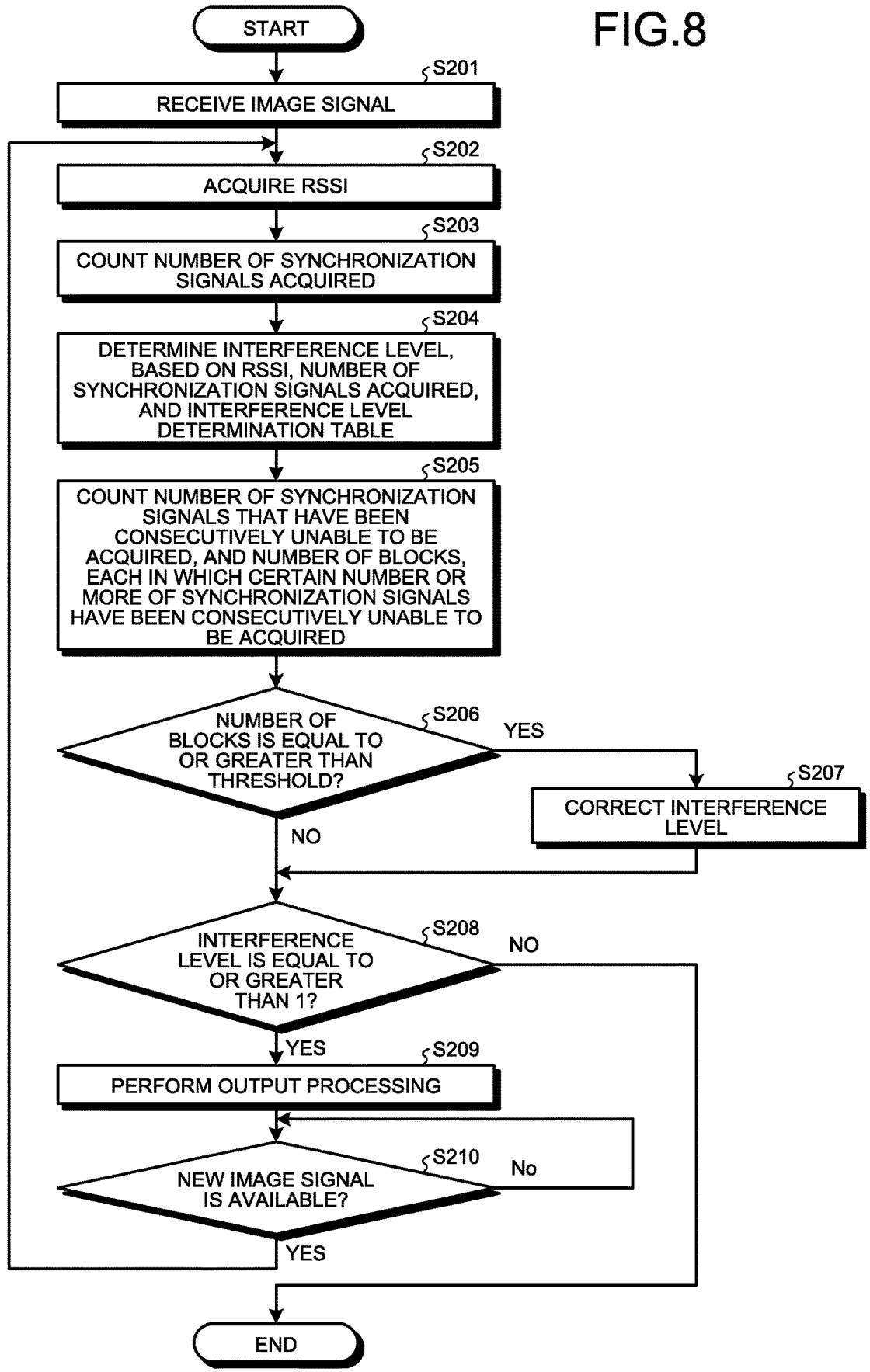
FIG. 8 is a flow chart illustrating interference level determination processing performed by a receiving device of the capsule-type endoscope system according to the modified example of the first embodiment.

Next, interference level determination processing executed by the receiving device 4A will be described. FIG. 8 is a flow chart illustrating the interference level determination processing performed by the receiving device of the capsule-type endoscope system according to the modified example of the first embodiment. Firstly, at Step S201, the receiving unit 401 receives an image signal.

At Step S202 subsequent to Step S201, the reception strength measuring unit 402 measures a received signal strength indicator at the time of the reception of the image signal by the receiving unit 401. The reception strength measuring unit 402 outputs the measured received signal strength indicator, to the determining unit 404A.

At Step S203 subsequent to Step S202, the synchronization signal counting unit 403 counts synchronization signals included in the image signal. The synchronization signal counting unit 403 outputs the number of synchronization signals acquired, to the determining unit 404A. The order of Step S202 and Step S203 is not limited to the above described order, and thus Step S203 may be performed before Step S202, or Step S202 and Step S203 may be performed simultaneously.

At Step S204 subsequent to Step S203, the determining unit 404A determines an interference level between the capsule-type endoscope 2 and the receiving antenna unit 3, based on: a received signal strength indicator measured by the reception strength measuring unit 402; the number of synchronization signals (the number of synchronization signals acquired) counted by the synchronization signal counting unit 403; and the interference level determination table illustrated in FIG. 3.

Thereafter, the NG counting unit 404a counts the number of synchronization signals that have been consecutively unable to be acquired, and the number of blocks, each in which a certain number or more of synchronization signals have been consecutively unable to be acquired (Step S205).

At Step S206 subsequent to Step S205, the determining unit 404A compares the number of times the state $S_{NG}$ lasted consecutively and the number of blocks $G_N$, each in which the state $S_{NG}$ lasted consecutively for a certain number of times or more, the numbers having been counted by the NG counting unit 404a, with preset thresholds.

If the determining unit 404A determines that the number of times the state $S_{NG}$ lasted consecutively and the number of blocks $G_N$, each in which the state $S_{NG}$ lasted consecutively for a certain number of times or more are less than the thresholds (Step S206: No), the control unit 409 proceeds to Step S208. On the contrary, if the determining unit 404 determines that the number of times the state $S_{NG}$ lasted consecutively and the number of blocks $G_N$, each in which the state $S_{NG}$ lasted consecutively for a certain number of times or more are equal to or greater than the thresholds (Step S206: Yes), the control unit 409 proceeds to Step S207.

At Step S207, the determining unit 404A performs correction of the interference level. The determining unit 404A adds, for example, a preset correction value to the determined interference level. Plural correction values may be set beforehand according to the numbers of consecutive NG groups, and the determining unit 404A may add a correction value according to the number of times the state $S_{NG}$ lasted consecutively, and the number of blocks $G_N$, each in which the state $S_{NG}$ lasted for a certain number of times or more, to the determined interference level. After the correction of the interference level is completed, the control unit 409 proceeds to Step S208.

At Step S208, a control unit 209 determines whether or not the interference level is equal to or greater than 1. If the interference level is less than 1 (Step S208: No), the control unit 409 ends the interference level determination processing for the image signal.

On the contrary, if the interference level is equal to or greater than 1 (Step S208: Yes), the control unit 409 proceeds to Step S209.

At Step S209, the control unit 409 causes the output unit 407 to perform output processing. Under control by the control unit 409, the output unit 407 displays a notification image, or generates sound, light, or vibration, according to the interference level.

At Step S210 subsequent to Step S209, the control unit 409 determines whether or not a new image signal is available. Specifically, the control unit 409 determines whether or not the receiving unit 401 has received a new image signal. If a new image signal is not available (Step S210: No), the control unit 409 repeats the check for an image signal. On the contrary, if a new image signal is available (Step S210: Yes), the control unit 409 proceeds to Step S202, and performs the above described interference level determination processing for the new image signal.

By the above described determination processing, the subject H having the capsule-type endoscope 2 introduced therein is able to be guided to a place where electromagnetic interference does not occur.

According to the above described modified example of the first embodiment, since the determining unit 404A determines an interference level between the capsule-type endoscope 2 and the receiving antenna unit 3, based on a received signal strength indicator measured by the reception strength measuring unit 402, the number of synchronization signals acquired counted by the synchronization signal counting unit 403, and the interference level determination table, and corrects the interference level according to a state of acquisition of the synchronization signals; as compared with the above described first embodiment, interference in communication between the capsule-type endoscope 2 and the receiving device 4A is able to be avoided even more. Even if the number of synchronization signals acquired corresponding to a low interference level has been achieved, if synchronization signals have been consecutively unable to be acquired, there is a risk that interference may have occurred. According to this modified example, by weighting of the determined interference levels according to the consecutive NG counts or groups (the number of blocks), interference is able to be avoided even more infallibly.

Second Embodiment

Figure 9:
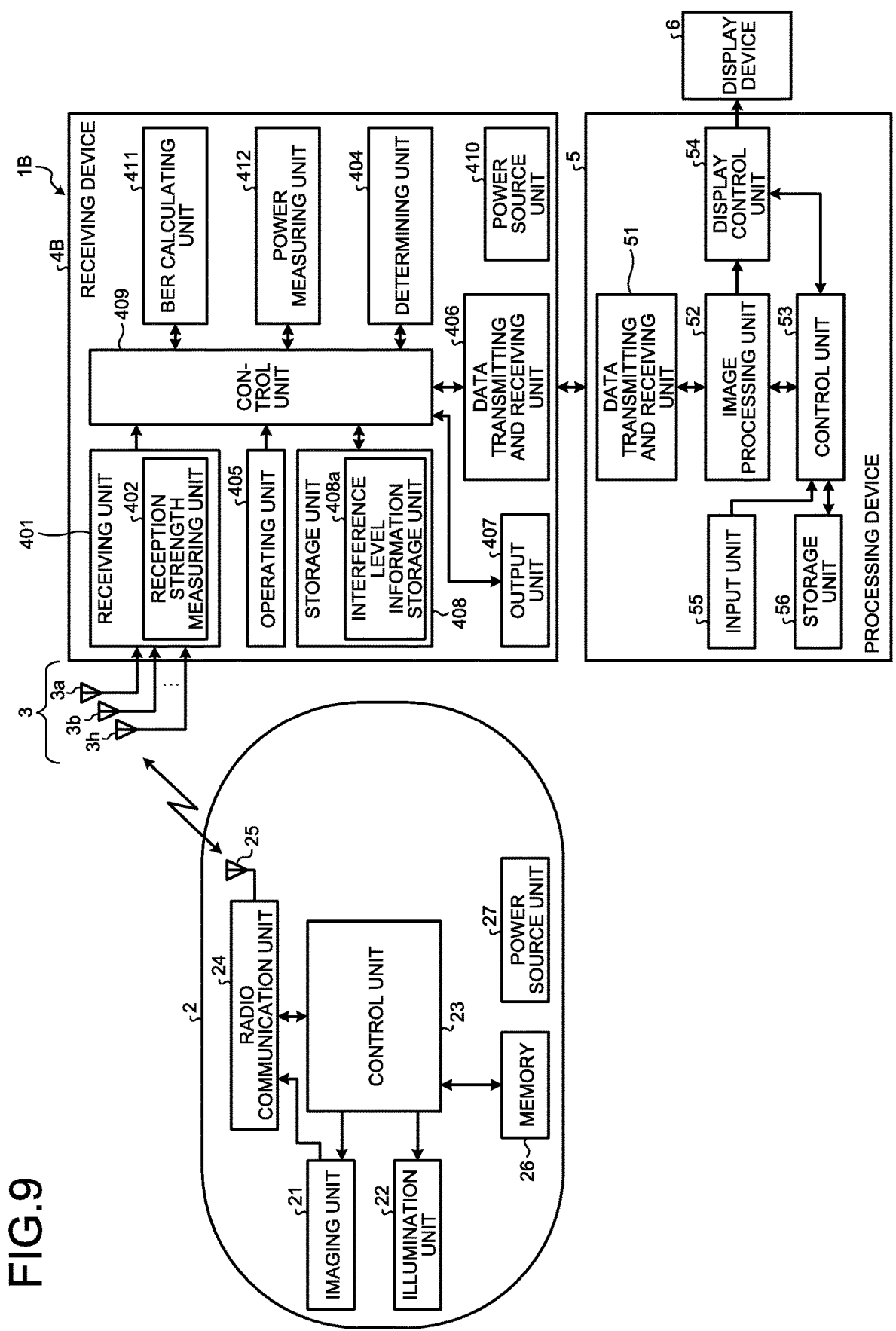
FIG. 9 is a block diagram illustrating a schematic configuration of a capsule-type endoscope system according to a second embodiment.

Next, a second embodiment will be described. FIG. 9 is a block diagram illustrating a schematic configuration of a capsule-type endoscope system according to the second embodiment.

A capsule-type endoscope system 1B according to the second embodiment includes: the capsule-type endoscope 2; a receiving device 4B that receives, via the receiving antenna unit 3 including the plural receiving antennas 3a to 3h attached to the subject H, a radio signal transmitted from the capsule-type endoscope 2; and the processing device 5 that fetches an image signal captured by the capsule-type endoscope 2 via the cradle 5a, processes the image signal, and generates an in-vivo image of the subject H. The image generated by the processing device 5 is, for example, output from the display device 6 by being displayed thereon.

The receiving device 4B includes, among the above described components of the receiving device 4, a bit error rate (BER) calculating unit 411 and a power measuring unit 412, instead of the synchronization signal counting unit 403. According to this second embodiment, a received signal strength indicator measured by the reception strength measuring unit 402 is used for selection from the receiving antennas 3a to 3h, and is not used for determination of an interference level.

The BER calculating unit 411 calculates a bit error rate (BER) by using an image signal received by the receiving unit 401. By dividing the number of bits with errors generated therein by the total number of bits, the BER calculating unit 411 calculates the BER. The BER may be calculated from the number of error bits of a fixed pattern (for example, a synchronization signal) that has ben embedded in the image signal. The BER calculating unit 411 is formed of a CPU or an ASIC.

The power measuring unit 412 measures a received power (dBm) by using the image signal received by the receiving unit 401. From the received signal strength indicator received by one of the receiving antennas 3a to 3h that has acquired the image signal, a power measuring unit 42 measures the received power (dBm). According to this second embodiment, this received power corresponds to a received signal strength indicator according to the present disclosure. The power measuring unit 412 corresponds to a strength acquiring unit according to the present disclosure. The power measuring unit 412 is formed of a CPU or an ASIC. The power measuring unit 412 may be provided in the receiving unit 401.

Figure 10:
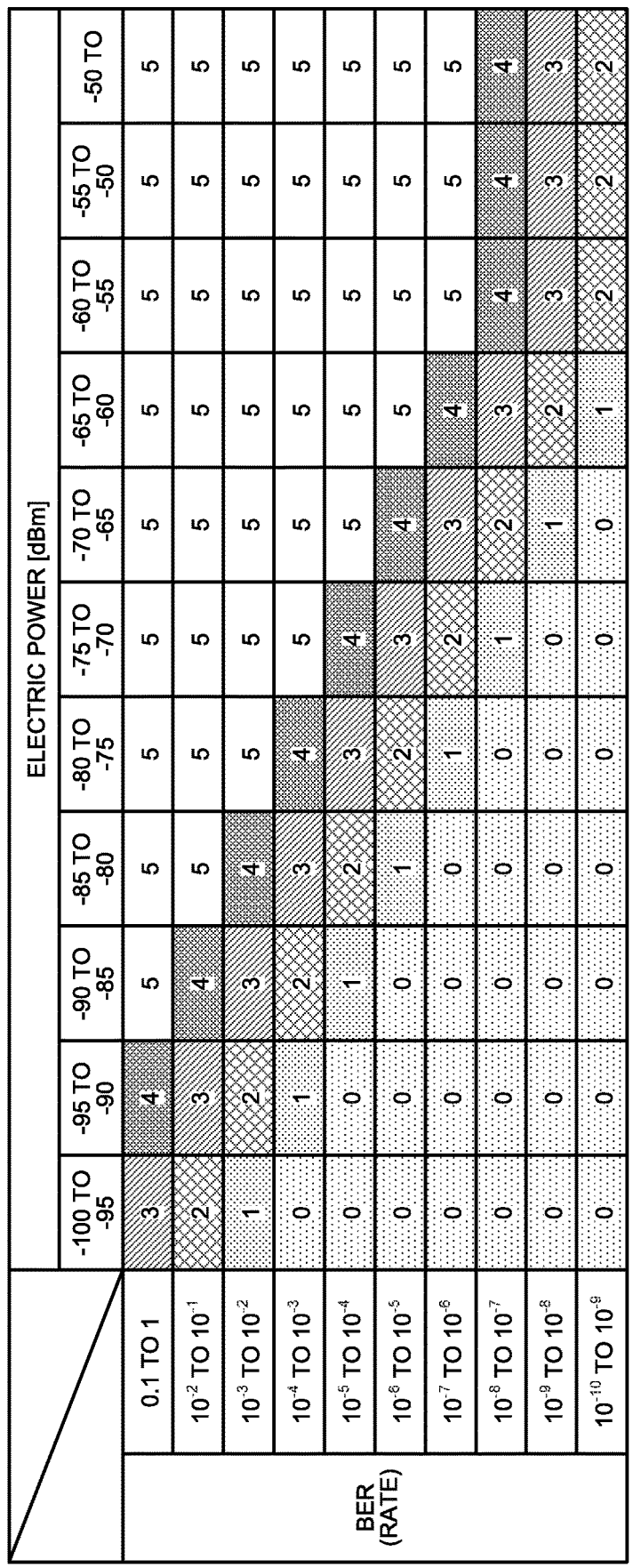
FIG. 10 is a diagram for explanation of an interference level determination table stored in a storage unit of the capsule-type endoscope system according to the second embodiment.

An interference level determination table stored in the interference level information storage unit 408a according to the second embodiment will now be described by reference to FIG. 10. FIG. 10 is a diagram for explanation of the interference level determination table stored in the storage unit of the capsule-type endoscope system according to the second embodiment. The interference level determination table represents, as illustrated in FIG. 10, an interference level distribution determined by bit error rates (BERs) and received powers. The interference level determination table is generated beforehand, based on interference levels determined by BERs and received powers that have been measured in advance. The receiving device 4B may be configured to: be able to transmit a signal for determination, the signal having a known bit string; receive the signal for determination transmitted by itself; calculate a BER for each received power; and generate the interference level determination table; or the interference level determination table may be generated based on BERs measured by a measurer that is different from the receiving device 4B and received powers upon those measurements.

Based on the BER calculated by the BER calculating unit 411, the received power measured by the power measuring unit 412, and the interference level determination table illustrated in FIG. 10, the determining unit 404 determines an interference level between the capsule-type endoscope 2 and the receiving antenna unit 3.

Figure 11:
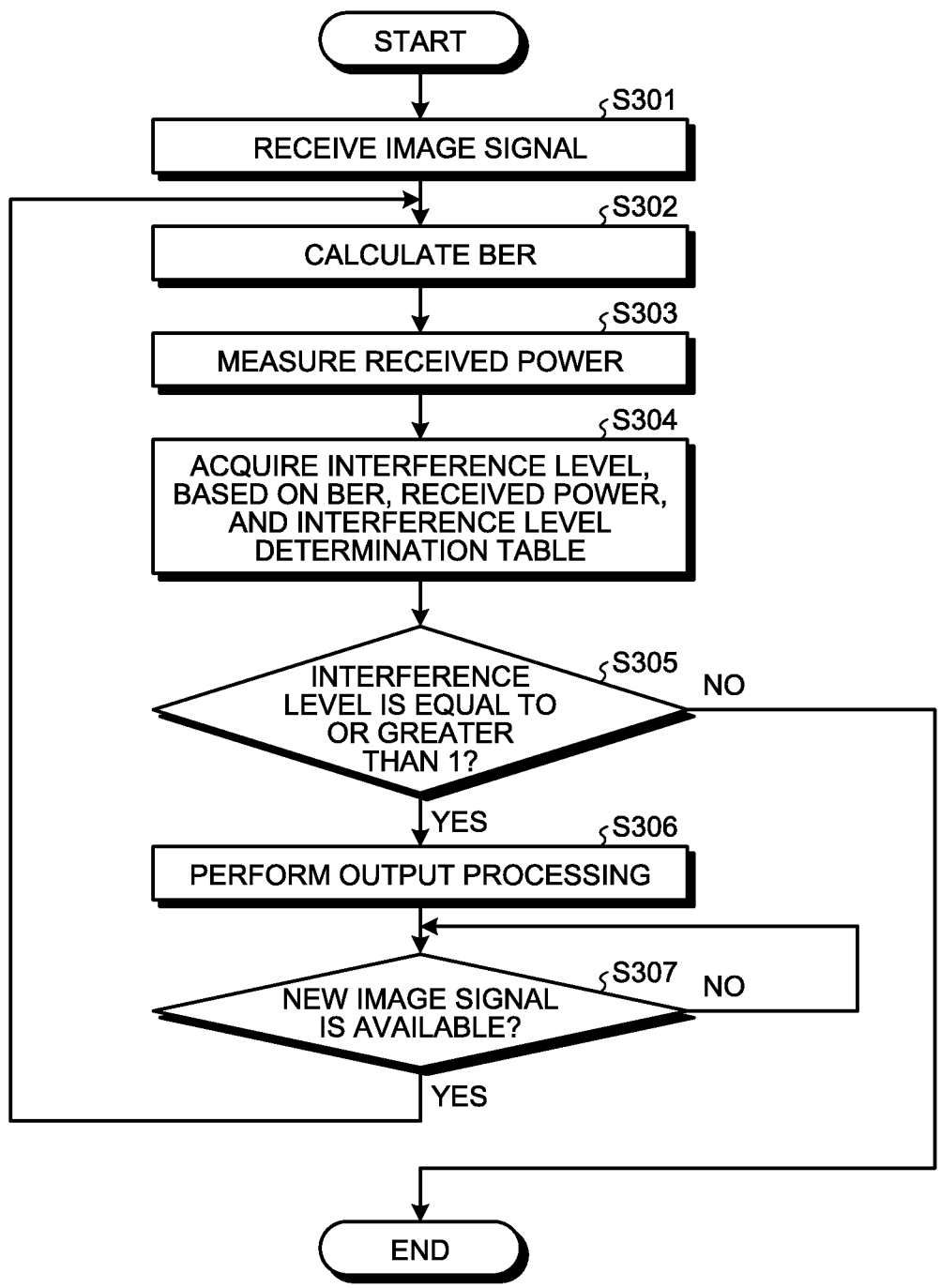
FIG. 11 is a flow chart illustrating interference level determination processing performed by a receiving device of the capsule-type endoscope system according to the second embodiment.

Next, interference level determination processing executed by the receiving device 4B will be described. FIG. 11 is a flow chart illustrating the interference level determination processing performed by the receiving device of the capsule-type endoscope system according to the second embodiment of the present disclosure. Firstly, at Step S301, the receiving unit 401 receives an image signal.

At Step S302 subsequent to Step S301, the BER calculating unit 411 calculates a bit error rate (BER) by using the image signal received by the receiving unit 401. The BER calculating unit 411 outputs the calculated bit error rate, to the determining unit 404.

At Step S303 subsequent to Step S302, the power measuring unit 412 measures a received power by using the image signal received by the receiving unit 401. The power measuring unit 412 outputs the measured received power, to the determining unit 404. The order of Step S302 and Step S303 is not limited to the above described order, and thus Step S303 may be performed before Step S302, or Step S302 and Step S303 may be performed simultaneously.

At Step S304 subsequent to Step S303, the determining unit 404 determines an interference level between the capsule-type endoscope 2 and the receiving antenna unit 3, based on the BER calculated by the BER calculating unit 411, the received power measured by the power measuring unit 412, and the interference level determination table illustrated in FIG. 10.

At Step S305 subsequent to Step S304, the control unit 409 determines whether or not the interference level is equal to or greater than 1. If the interference level is less than 1 (Step S305: No), the control unit 409 ends the interference level determination processing for the image signal.

On the contrary, if the interference level is equal to or greater than 1 (Step S305: Yes), the control unit 409 proceeds to Step S306.

At Step S306, the control unit 409 causes the output unit 407 to perform output processing. Under control by the control unit 409, the output unit 407 displays a notification image, or generates sound, light, or vibration, according to the interference level.

At Step S307 subsequent to Step S306, the control unit 409 determines whether or not a new image signal is available. Specifically, the control unit 409 determines whether or not the receiving unit 401 has received a new image signal. If a new image signal is not available (Step S307: No), the control unit 409 repeats the check for an image signal. On the contrary, if a new image signal is available (Step S307: Yes), the control unit 409 proceeds to Step S302, and performs the above described interference level determination processing for the new image signal.

By the above described determination processing, the subject H having the capsule-type endoscope 2 introduced therein is able to be caused to avoid the place where the electromagnetic interference has occurred.

According to the above described second embodiment, since the determining unit 404 determines, based on a BER calculated by the BER calculating unit 411, a received power measured by the power measuring unit 412, and the interference level determination table, an interference level between the capsule-type endoscope 2 and the receiving antenna unit 3, and gives notification to the subject H based on a result of the determination; interference in communication between the capsule-type endoscope 2 and the receiving device 4B is able to be avoided. Thereby, the number of errors in images generated from image signals wirelessly transmitted from the capsule-type endoscope 2 is able to be reduced, and thus accuracy of diagnoses is able to be improved.

Thus far, modes for carrying out the present disclosure have been described, but the present disclosure is not limited only to the above described embodiments and modified example. Without being limited to the above described embodiments and modified example, the present disclosure may include various embodiments without departing from the technical ideas stated in the claims. Further, the components according to the embodiments and modified example may be combined as appropriate.

According to the above description of the first and second embodiments, an interference level is determined to be any of 0 to 5 by use of the interference level determination table: but not being limited to these embodiments, an interference level may be determined to be any of two levels, 0 and 1, that is, whether or not interference has occurred may be determined; or not being limited to the six levels of 0 to 5, an interference level distribution may be set in a preset number of levels in an interference level determination table.

Further, according to the above description of the first and second embodiments, an interference level is determined by use of the interference level determination table, but not being limited to a table, a function may be generated beforehand, and the determining unit 404 may calculate an interference level by, for example, inputting a received signal strength indicator and the number of synchronization signals acquired, or a bit error rate and a received power, into the function.

Further, in the above described first embodiment, the interference level determination table illustrated in FIG. 3 may be generated from correspondence between the numbers of synchronization signals acquired and the BER characteristics according to the second embodiment. In this case, the synchronization signal counting unit 403 counts the number of synchronization signals acquired, and the determining unit 404 determines an interference level determined based on RSSI and the number of synchronization signals that is determined from the BER.

Further, the execution program for the processing executed by each component of the capsule-type endoscope 2, the receiving device 4, and the processing device 5, of the capsule-type endoscope system 1 according to the first or second embodiment may be configured to be recorded and provided, in a file having an installable format or an executable format, on a computer readable recording medium, such as a CD-ROM, a flexible disc (FD), a CD-R, or a DVD; or may be configured to be provided by being stored on a computer connected to a network, such as the Internet, and being downloaded via the network. Furthermore, the execution program may be configured to be provided or distributed via a network, such as the internet.

The present disclosure has an effect of enabling avoidance of interference in communication between an image acquisition device and a receiving device.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus, comprising:
an antenna configured to receive, by a radio wave, an image signal acquired by a capsule-type endoscope;
a memory configured to store a determination table or a determination function, each being used for determining an interference level of the radio wave; and
a processor comprising hardware, the processor is configured to:
  acquire a received signal strength of the image signal received by the antenna;
  generate determination information used for determining the interference level of the radio wave based on one or more synchronization signals included in the image signal;
  determine the interference level of the radio wave based on the received signal strength and the determination information by using the determination table or the determination function; and
  control to output information indicating that electromagnetic interference occurs, when the determined interference level of the radio wave is greater than a preset interference level;
wherein the processor generates, as the determination information, the number of synchronization signals by counting the synchronization signals included in the image signal.

2. The receiving apparatus according to claim 1, wherein the image signal is a signal generated by pixels arranged in a matrix,
the image signal includes the one or more synchronization signals for each set of line data corresponding to a horizontal line in the arrangement of the pixels, and
the processor
  determines an interference level of the radio wave based on the received signal strength and the number of synchronization signals,
  determines whether the synchronization signals included in the image signal are acquired for the each set of line data, and
  compensates the interference level when determination results indicating absence of the synchronization signals occur consecutively in the order of the sets of line data.

3. A receiving apparatus, comprising:
an antenna configured to receive, by a radio wave, an image signal acquired by a capsule-type endoscope;
a memory configured to store a determination table or a determination function, each being used for determining an interference level of the radio wave; and
a processor comprising hardware, the processor is configured to:
  acquire a received signal strength of the image signal received by the antenna;
  generate determination information for determining an interference level of the radio wave based on the number of error bits caused by interference to the radio wave during communication, the error bits occurring in the image signal received by the antenna or in a fixed pattern embedded in the image signal,
  determine the interference level of the radio wave based on the received signal strength and the determination information by using the determination table or the determination function; and
  control to output information indicating that electromagnetic interference occurs, when the determined interference level of the radio wave is greater than a preset interference level;
wherein the processor calculates, as the determination information, a bit error rate from the number of error bits.

4. The receiving apparatus according to claim 3, wherein the processor
  generates, as the determination information, the number of synchronization signals by counting the synchronization signals included in the image signal, and
  determines an interference level of the radio wave that is determined based on: the number of synchronization signals obtained from the bit error rate; and the received signal strength.

5. The receiving apparatus according to claim 1, further comprising one or more antennas besides said antenna, wherein the processor acquires a received signal strength of one of all antennas, whose received signal strength of an image signal is the largest.

6. A radio wave interference determination method, comprising:
- receiving, by an antenna with a radio wave, an image signal acquired by a capsule-type endoscope, and acquiring a received signal strength of the image signal;
- generating determination information used for determining the interference level of the radio wave based on one or more synchronization signals included in the image signal;
- determining the interference level of the radio wave based on the received signal strength and the determination information by using a determination table or a determination function, each being stored in a memory and being used for determining the interference level of the radio wave; and
- outputting information indicating that electromagnetic interference occurs, when the determined interference level of the radio wave is greater than a preset interference level;
- wherein the determination information is generated by the number of synchronization signals by counting the synchronization signals included in the image signal.

7. A radio wave interference determination method, comprising:
- receiving, by an antenna with a radio wave, an image signal acquired by a capsule-type endoscope, and acquiring a received signal strength of the image signal;
- generating determination information for determination determining an interference level of the radio wave based on the number of error bits caused by interference to the radio wave during communication, the error bits occurring in the image signal received by the antenna or in a fixed pattern embedded in the image signal,
- determining the interference level of the radio wave based on the received signal strength and the determination information by using a determination table or a determination function, each being stored in a memory and being used for determining the interference level of the radio wave; and
- outputting information indicating that electromagnetic interference occurs, when the determined interference level of the radio wave is greater than a preset interference level;
- wherein the determination information is generated by a bit error rate from the number of error bits.

* * * * *